United States Patent [19]

Ellison et al.

[11] Patent Number: Plant 6,623

[45] Date of Patent: Feb. 21, 1989

[54] ASPARAGUS PLANT NAMED JERSEY JADE

[75] Inventors: J. Howard Ellison, Milltown; John J. Kinelski, Princeton, both of N.J.

[73] Assignee: Rutgers University, New Brunswick, N.J.

[21] Appl. No.: 77,522

[22] Filed: Jul. 6, 1987

[51] Int. Cl.[4] ..... A01H 5/00

[52] U.S. Cl. ..... Plt./89

[58] Field of Search ..... Plt./89

*Primary Examiner*—Robert E. Bagwill

*Attorney, Agent, or Firm*—Frank B. Robb

[57] ABSTRACT

A female asparagus hybrid carrying the persistent green marker gene "gg", which results in the retention of the green color in the fall until the plant is killed by freezing, the plant further having tolerance to rust (*Puccinia asparagi*) *Fusarium oxysporum* (root rot) and *Fusarium moniliforme* (crown rot), being long lived and producing high yield of good quality spears.

1 Drawing Sheet

1

The invention described herein and in detail relating to a new variety of asparagus plant includes data which has been assembled with regard to this plant over a substantial period of time. Our new variety is one of many varieties which we have developed and are continuing to develop, the plant itself originating from a field of Mary Washington (unpatented) in South New Jersey. It is and notable for having tolerance to rust (*Puccinia asparagi*), *Fusarium oxysporum* (root rot) and *Fusarium noniliforme* (crown rot), and important for its high yield of good quality spears.

The object of these developments and of our program is to produce plants which have increased yields as well as larger, longer spears. The color of the plant itself is distinctive by reason of its dark green foliage in late summer and fall with a complete absence of yellow pigmentation.

We have chosen to denominate the instant variety as "Jersey Jade" and further identify the same in our records by the No. 61.

In the course of our experiments and development of asparagus, we have noted certain aspects which uniformly appear in certain varieties and in particular in the instant variety "Jersey Jade", we note that the chlorophyll content which we have measured during the course of our development is in this instance 3.814 milligrams per gram fresh weight, and the yellow control 1.621 milligram per gram fresh weight.

Our new variety has been reproduced both by crown division and by tissue culture and found to retain its distinguishing characteristics from generation to generation and to come true.

Figure 2:
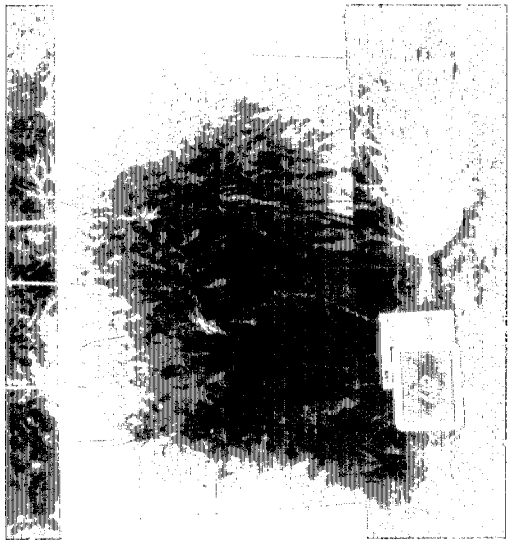
Figure 1:
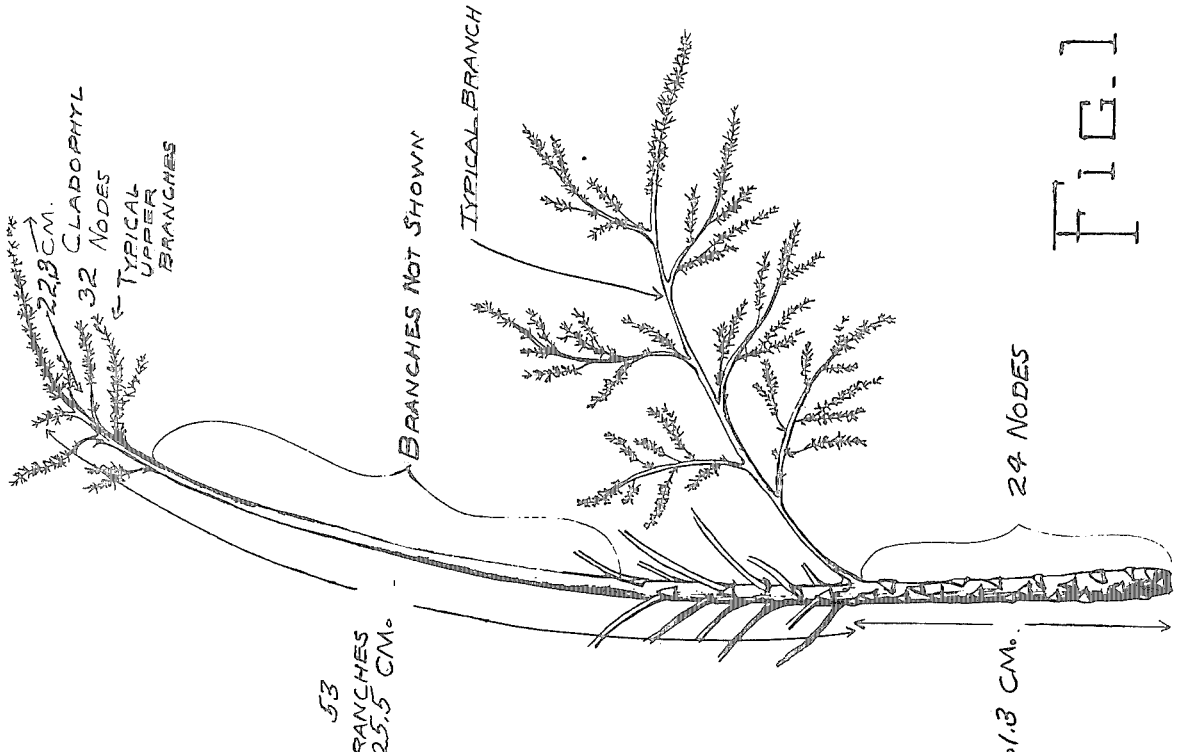

In the drawing attached hereto we have applied certain data to a typical stalk of a plant of our new variety which is observed in FIG. 1 and in FIG. 2 a color photograph of the plant as it appears in fall is shown.

We note that the color descriptions where used in the data supplied and included herein, provide details of a typical plant as representative as it is possible to make the same in a color illustration of an asparagus plant. The illustration was made from a photograph taken under normal field conditions on a day of average sunlight.

The references to a color scale are those of the Munsell Limit Color Cascade published by Macbeth Color and Photometry Division of Baltimore, Md., the numbers coinciding with those applied thereto.

2

We have caused our new variety "Jersey Jade" to be asexually reproduced in the vicinity of New Brunswick, New Jersey and find that it comes true in successive generations.

The data supplied herewith enable the plant of our new variety to be compared with the prior plants of other origin and will be noted in comparison with other patents which we have obtained noting that the data support the fact that there is an improvement and certainly an identifiable difference between this plant and those previously the subject matter of patent.

It is noted that the data are applied to the typical stalk illustrated and are representative of our new variety.

ASPARAGUS PLANT NO. 61 Female "Jersey Jade"
Inch × 2.54 = cm.

| | |
|---|---|
| Stalk Data | |
| Number of nodes below first branch | 24 |
| Number of cm from crown to first branch | 61.3 |
| Number of branches | 53 |
| Number cm between first and last branch | 125.5 |
| Internode length in cm between branches | 2.37 |
| Number of cladophyll nodes beyond last branch | 32 |
| Number of cm beyond last branch | 22.3 |
| Internode length in cm beyond last branch | 0.70 |
| (Note-all above are largest stalk) | |
| Largest stalk diameter in mm | 30.0 |
| Mean diameter of three largest stalks in mm | 29.1 |
| Number of stalks | 25 |
| Stalk vigor index | 21.170 |
| Mature stalk color, bloom removed. Color No. 1 | 22-14 |
| Yellow control = | 28.8 |
| Crown to first branch of highest headed stalk | 58.4 cm. |
| Flower Data | |
| Petal tip (yellow) Color No. (1) | 25-4.5 |
| Petal base (green) Color No. (1) | 23-8 |
| Flower length (mm) | 4.1 |
| Flower width at midpoint in mm. | 2.3 |
| Fruit Data (61 × 22-8) | |
| Weight of 100 fruit (g) | 24.2 |
| Water displacement of 100 fruit (ml) | 27.0 |
| Number of seed per 100 fruit | 192 |
| Weight of seed per 100 fruit (g) | 8.0 |
| Mean weight per seed (g) | 0.0417 |
| Water displacement of seed of 100 fruit (ml) | 8.0 |
| Mature fruit Color No. (1) | 33-13 |
| Cladophyll Data | |
| Number per node | 4.83 |
| Length (mm) | 16.1 |
| Width (mm) | 0.155 |
| Chlorophyll Data | |
| Chlorophyll content 11-5-84 | mg. per gm. fresh wt. |

-continued

| ASPARAGUS PLANT NO. 61 Female "Jersey Jade" Inch × 2.54 = cm. | |
|---|---|
| Jersey Jade | 3.814 |
| Yellow control | 1.621 |

We claim:

1. A new and distinct variety of asparagus plant as herein shown and described, characterized particularly as to novelty by the unique combination of a female variety of substantial chlorophyll content, tolerance to rust (*Puccinia asparagi*), *Fusarium oxysporum* (root rot), and *Fusarium moniliforme* (crown rot), is long lived, producing high yields of good quality spears, retaining the dark green foliage through late summer and fall with a complete absence of yellow pigmentation, and carrying the persistent green marker gene "gg".

* * * * *